United States Patent
Hellberg

(10) Patent No.: US 6,918,936 B2
(45) Date of Patent: Jul. 19, 2005

(54) THERMOPLASTIC LINER BLANK

(76) Inventor: Kennet Hellberg, Morbylundsvagen 40, Vallentuna (SE), S-186 33

(\*) Notice: Subject to any disclaimer, the term of this patent is extended or adjusted under 35 U.S.C. 154(b) by 131 days.

(21) Appl. No.: 10/180,085

(22) Filed: Jun. 27, 2002

(65) Prior Publication Data

US 2002/0165619 A1 Nov. 7, 2002

Related U.S. Application Data

(63) Continuation-in-part of application No. 09/403,077, filed as application No. PCT/SE98/00543 on Mar. 25, 1998, now Pat. No. 6,440,345.

(30) Foreign Application Priority Data

Apr. 29, 1997 (SE) .................................... 9701619

(51) Int. Cl.⁷ .................................................. A61F 2/80
(52) U.S. Cl. .............................. 623/36; 623/27; 623/57; 623/926
(58) Field of Search ........................ 264/222, DIG. 30; 623/27, 33, 36, 57

(56) References Cited

U.S. PATENT DOCUMENTS

| | | | | |
|---|---|---|---|---|
| 4,473,421 A | | 9/1984 | Gustafsson | |
| 4,562,882 A | * | 1/1986 | Alleluia | 164/529 |
| 4,685,453 A | | 8/1987 | Guignard et al. | |
| 4,696,780 A | | 9/1987 | Hägglund | |
| 4,704,129 A | * | 11/1987 | Massey | 623/25 |
| 4,735,754 A | * | 4/1988 | Buckner | 264/40.1 |
| 5,376,129 A | * | 12/1994 | Faulkner et al. | 623/33 |
| 5,376,132 A | | 12/1994 | Caspers | |
| 5,603,122 A | | 2/1997 | Kania | |
| 5,662,715 A | | 9/1997 | Slemker | |
| 5,728,168 A | * | 3/1998 | Laghi et al. | 623/36 |
| 5,830,237 A | | 11/1998 | Kania | |
| 5,888,231 A | * | 3/1999 | Sandvig et al. | 623/36 |
| 6,030,418 A | * | 2/2000 | Biedermann | 623/36 |
| 6,406,499 B1 | * | 6/2002 | Kania | 623/36 |
| 6,440,345 B1 | * | 8/2002 | Hellberg | 264/222 |

FOREIGN PATENT DOCUMENTS

| | | |
|---|---|---|
| GB | 2104386 | 3/1983 |
| SE | 434928 | 8/1984 |
| SE | 454943 | 6/1988 |
| WO | 9703819 | 2/1997 |

\* cited by examiner

Primary Examiner—Paul B. Prebilic
(74) Attorney, Agent, or Firm—Young & Thompson

(57) ABSTRACT

A soft and elastic prosthetic liner blank for customizing to an individual user is formed from thermoplastic material and molded to a hollow, generally rotation symmetric shape having at least one radial dimension. The liner blank has an open proximal end for insertion of the residuum of an amputee's arm or leg and a closed distal end, and the liner blank further having a material composition allowing thermo-forming of the liner blank while maintaining elasticity in the thermally applied shape. The radius of the liner blank is dimensioned to accommodate and to adopt, through plastic deformation, any sectional profile included in the positive copy.

11 Claims, 4 Drawing Sheets

THERMOPLASTIC LINER BLANK

Continuation-in-part of U.S. patent application Ser. No. 09/403,077, filed Oct. 15, 1999, now U.S. Pat. No. 6,440,345.

BACKGROUND

The present invention relates to a soft and elastic prosthetic sleeve, and more exactly to a liner blank provided for customizing through thermoplastic deformation and adaptation to the individual wearer of a prosthetic device.

In connection with amputation of an extremity, i.e. a leg or an arm, an amputation stump or residuum often remains to serve for attachment of a prosthetic device. The amputation stump is inserted into a rigid sleeve or socket that forms an attachment for the prosthetic device, which for example may be a foot or a lower leg with foot in case the stump is situated below the knee of a leg. Similarly, the prosthesis may be an entire prosthetic leg, whereby a remaining portion of the thighbone is fitted into a corresponding prosthetic socket. A lower arm or upper arm prosthesis may be attached in a corresponding way to a hand or arm prosthetic device.

The socket often has a generally conical shape, one end of which is open and the other being completely closed and having a somewhat rounded off shape. Additionally, the socket may be adapted to the shape of the amputation stump. Prosthetic devices consequently confines what is left of the extremity in a specially adapted socket attached to the prosthesis, the socket transferring forces between the prosthesis and the remaining portion of the extremity.

An individually adapted socket is manufactured by producing a copy of what is left of the extremity. Today there are mainly two methods utilized to do this, either a laser scanner is used which is imaging the body portion to be copied, then the values read by the scanner are transferred to a milling cutter that mills a copy of the body portion, or a negative plaster cast is made by means of plaster bandage, where after the negative plaster cast is filled to create a positive copy of the body portion. Then by means of the positive copy a rigid prosthetic socket is molded for a close fit about the amputation stump. A disadvantage with such copies is that they are true copies only at the time of the plaster casting. The reason for this is that the human body is continuously changing and especially then the portion left of an amputated extremity, the atrophy being large (in time it decreases in volume).

The problem of the rigid socket is that it does not follow the changes in volume, and the remains of the extremity is soft and sensitive while the socket member is hard, which may result in the extremity being chafed if there is not a softer sleeve or liner inside the socket. Therefore today different kinds of prosthetic socks or soft sleeves/liners are used inside the rigid outer sleeves/sockets.

U.S. Pat. No. 5,376,132 (Caspers) suggests a prosthetic liner and socket that is adapted to the shape of the residuum. A viscous fluid mixture of polymer components is introduced to set and cure in a spacing that is formed between a reduced positive model of the residuum, and an outer, negative mold. This method of forming the liner with socket in adaptation to the shape of the residuum is complex and involves a plurality of method steps a to k for molding the liner to the shape of the individual wearer.

U.S. Pat. No. 5,603,122 (Kania) suggests a form fitting sleeve member with a contoured form fit. A stretchable, elastic textile fabric is used for producing a form fit sock by sewing together two or three pieces of the material, cut into suitable patterns for a certain degree of adaptation to the shape of an amputation stump. The sock member is impregnated with polymeric material that provides a cushioning interface between the residuum and a rigid prosthetic socket.

Another prior art soft liner is one made of silicone and disclosed in SE 454 943 B. A drawback of this sleeve is that it is not able to be particularly adapted to the amputation stump. On the contrary, the sleeve is so elastic that it can encircle the amputation stump, but as no amputation stump in reality is shaped conically, there will be higher pressure and stress applied to the following portions of the amputation stump:

in areas where the diameter of the stump is larger than the silicone sleeve, which means that the surface pressure on the stump will be relatively higher in these areas compared to other areas;

in areas, where the stump has a small radius, e.g. a prominence due to underlying bone, which means that the surface pressure over the prominence locally increases when the elastic sleeve is tightened over the prominence.

See also example of FIG. 4, which illustrates a soft elastic sleeve rolled onto a stump of a lower leg amputee, illustrating how the distal tibia point creates a bone prominence on the left hand side of FIG. 4.

Not only the pressure at the exposed portions will increase, but with stretching of the sleeve in these more sensitive areas, a larger loss of entropy arises in the sleeve at these areas, in other words the molecule chains are stretched, which in turn decreases their mobility and the soft sleeve becomes harder in the sensitive areas.

Elastic materials harden when they are stretched, and an uneven stress will be encountered when the most expanded portions of the elastic sleeve are placed over the prominences, which results in discomfort and the user being chafed.

Most of the users of prosthetic devices are lower leg amputees and elderly persons, and therefore do sit for longer times also when wearing a prosthetic device. One problem of common soft sleeves is that they fold at the back of the knee when the knee is bent, which results in discomfort chafing and, in the worst case, that the flow of blood is obstructed and a so called stasis condition arises. Note in FIG. 4 how the sleeve is folded at its upper right portion.

Accordingly there is a need for a soft elastic liner that avoids the drawbacks discussed above and which provides a comfortable support of a prosthetic device.

SUMMARY

The present invention aims to avoid these and other drawbacks by providing a soft and elastic liner for customizing and adaptation to the individual wearer of a prosthetic device.

It is therefore an object of the present invention to provide a soft, elastic liner blank that is readily adaptable to the true shape of the residuum of an amputee's arm or leg by being thermoformed on a positive copy of the residuum.

It is another object of the present invention to provide a soft, elastic liner blank that allows thermoforming at temperatures above a service temperature, and which remains shape permanent in use at comfortable, indoor and outdoor temperatures.

Still another object of the present invention is to provide a soft, elastic liner blank that allows thermoforming while maintaining elasticity in the thermally applied shape after forming.

Yet another object of the present invention is to provide a soft, elastic liner blank that is readily reshaped in adaptation to changes in the shape of the residuum.

A further object of the present invention is to provide a soft, elastic liner blank that is dimensioned to accommodate, through thermoplastic deformation, the volumes of differently sized amputation stumps within a range of sizes.

Yet a further object of the present invention is to provide a soft, elastic liner blank that is readily customized to the shape of the residuum in a few and simple procedural steps.

The above and other objects will be met in a liner blank as defined by the accompanying claims.

Briefly, a soft and elastic prosthetic liner blank is provided for customizing to an individual user by thermoforming on a positive copy of the residuum of an amputee's arm or leg. The liner blank is formed from thermoplastic material suitable for molding and has a material composition allowing thermoforming of the liner blank at temperatures ranging from about +60° C. and above while maintaining elasticity in the thermally applied and remaining shape in use at service temperatures after forming. Further, the liner blank is molded to a hollow, generally rotation symmetric shape having at least one radial dimension, and having an open proximal end and a closed distal end. The radius of the rotation symmetric liner blank is dimensioned to accommodate the radii included in the positive copy, and the customized liner blank is imprinted with the shape and sectional profiles of the positive copy for adopting the shape of the residuum and applying an evenly distributed pressure about the residuum.

Further features, embodiments and advantageous developments of the liner blank are explained in the specification below.

SHORT DESCRIPTION OF DRAWINGS

Below the invention will be described in detail with reference to the accompanying, diagrammatic drawings wherein FIG. 1 shows an example of a prior art elastic sleeve in a non-user mode;

FIG. 2 illustrates the residuum of an amputated leg;

FIG. 3 demonstrates the prior art sleeve being donned onto the amputation stump of FIG. 2;

DETAILED DESCRIPTION OF THE INVENTION

A liner blank according to the present invention is manufactured from thermoplastic material and preferably from a thermoplastic elastomer material.

Figure 12:
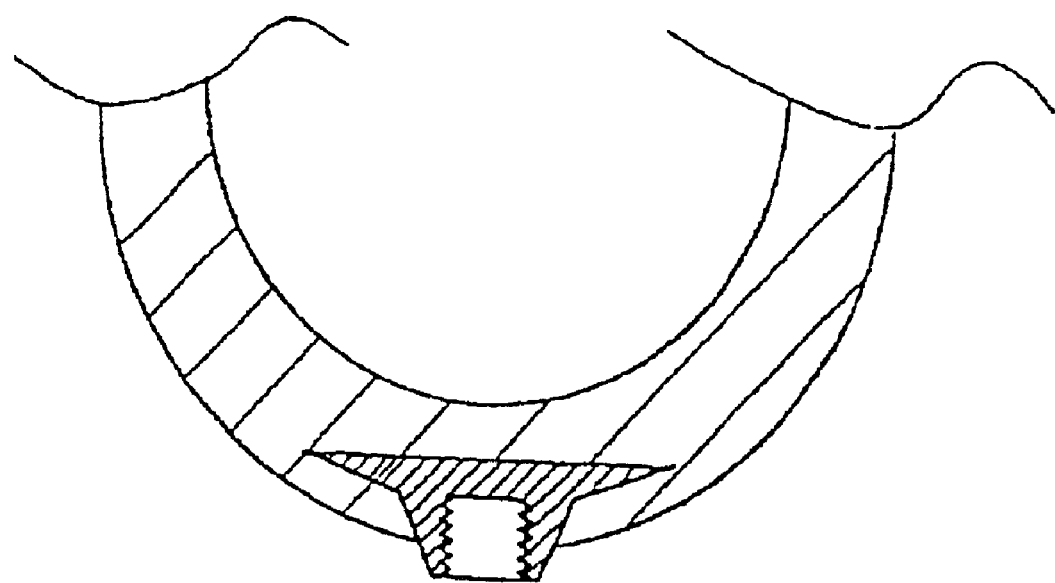
FIG. 12 is a partial section view showing the distal end of a liner blank and a coupling means embedded therein.

The liner blank has an open proximal end for insertion of a limb portion or residuum of an amputee's arm or leg, and the distal end is normally closed. The liner blank is molded to a hollow, seamless and generally rotation symmetric element having a radial dimension r. That is to be understood as a continuous radial dimension in the longitudinal direction of a cylinder shaped element. Alternatively, the liner blank may be molded to a cylinder with a conical taper towards the distal end, having a reducing radius r from the proximal end towards the distal end. The liner blank wall may be of equal thickness both circumferentially and longitudinally of the liner blank, or the wall may have a reducing thickness towards the open proximal end of the liner. The liner blank is rotation symmetric about a longitudinal center, and the outer periphery may be linearly or irregularly shaped and preformed as a liner blank for lower leg, upper leg, lower arm and upper arm soft liners, respectively, and for final customizing to the individual wearer. In the distal end, a coupling means (see FIG. 12) may be embedded for attachment to a rigid, outer socket that carries a prosthetic device.

The liner blank is a semi-finished product that is provided for customizing and adaptation to the individual wearer of a prosthetic device. Customizing the liner blank involves thermoforming on a copy of the amputated limb of the wearer.

Figure 7:
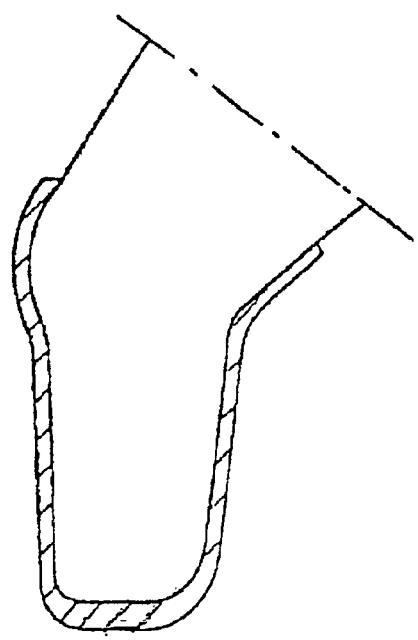
FIG. 7 shows the liner blank of the present invention applied onto a positive copy of the residuum.

In FIG. 7 of the drawings, a liner blank is applied over a positive copy of the amputated extremity. In the illustrated example, the copy corresponds to a knee with a lower leg stump. First, a casting is made of the body portion to be provided with a prosthetic device. This may be done by means of plaster bandage or alternatively by means of an imaging laser scanner. The hardened plaster bandage forms a negative mould of the residuum. The mould is then filled with plaster that becomes rigid and forms a positive copy of the residuum. Alternatively, a cutter controlled by a computer may in a suitable material create a copy of the residuum, aided by the data read by means of the laser scanner.

Figure 9:
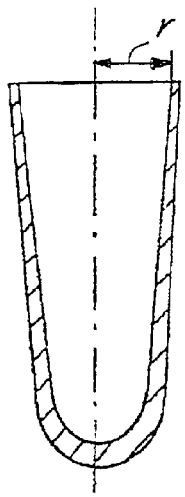
FIG. 9 illustrates a radius of a rotation symmetric liner blank dimensioned for thermoplastic expansion to adopt the customized shape.
Figure 10:
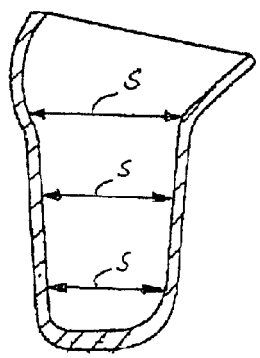
FIG. 10 illustrates sectional profiles in a thermally customized liner that has adopted the shape of the residuum.

As will be apparent to the eye when viewing FIGS. 9 and 10 of the drawings, the liner blank may be slightly under-dimensioned relative to the positive copy of the residuum. In other words, a radius r in any longitudinal position of the rotation symmetric liner blank is under-dimensioned relative to the radius in a corresponding position of the positive copy, i.e. relative to any sectional profile s included in the thermally customized liner as illustrated in FIG. 10, that is adapted to the shape of the residuum. Accordingly, the thermoplastic deformation and adaptation to the shape of the residuum will in this embodiment involve an expansion of the radial dimension or dimensions r, of the liner blank.

Figure 11:
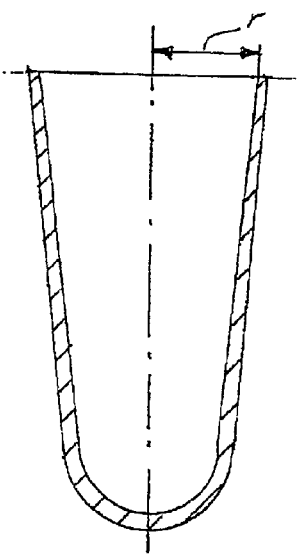
FIG. 11 illustrates a radius of a rotation symmetric liner blank dimensioned for thermoplastic contraction to adopt the customized shape.

Alternatively, the liner blank may be over-dimensioned relative to the positive copy of the residuum as illustrated in FIGS. 10 and 11. In other words, a radius r in any longitudinal position of the rotation symmetric liner blank is over-dimensioned relative to the radius in a corresponding position of the positive copy, i.e. relative to any sectional profile s included in the thermally customized liner as illustrated in FIG. 10, that is adapted to the shape of the residuum. Accordingly, the thermoplastic deformation and adaptation to the shape of the residuum involves in this embodiment a contraction of the radial dimension or dimensions r, of the liner blank.

Depending on the individual shape of the residuum, the thermoplastic deformation may involve expansion of the radial dimension/dimensions of the liner blank in a proximal portion thereof and contraction of the radius/radii in the distal portion, or vice versa. In each specific case, the liner blank is sized to have a radial dimension that accommodates, through plastic deformation, all radii that are included in the shape of the positive copy, and thus in the shape of the residuum.

Figure 8:
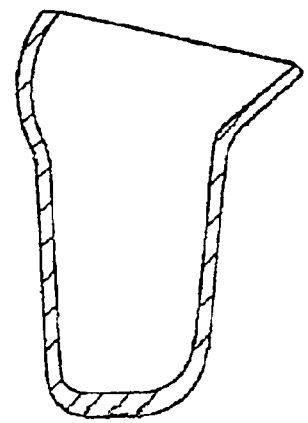
FIG. 8 illustrates the liner blank of FIG. 7 after removal of the positive copy, the liner maintaining the thermally applied shape after thermoplastic deformation to adopt the shape of the copy.

When applying the liner blank on the copy, care is taken for an accurate positioning of a coupling means, if present, in the distal end of the copy of the amputation stump. The liner blank is then rolled onto the copy, eventually causing in some areas a tensioning of the elastic material that circumferentially encloses the copy. The copy and liner blank are heated in a suitable manner, for instance in an oven, to a temperature of about +60° C. or more as required for thermoplastic deformation of the liner blank. When sufficient heat has been applied, any tensioning is relieved and the liner blank conforms to the shape of the positive copy through expansion and/or through contraction, adopting the shape of the residuum as is illustrated in FIGS. 8 and 10. When the liner cools it may crimp slightly, but the thermally applied shape is maintained as the thermally customized liner then is removed from the copy of the extremity. This will provide the best comfort for the user of the soft liner as the uneven distribution of pressure and folding demonstrated in FIG. 4 will be avoided, and which normally is observed in connection with non-customized socks and liners.

The material composition preferred for producing the liner blank is a thermoplastic elastomer based on styrene such as a Styrene-Ethylene/Butadiene-Styrene Blockcopolymer (SEBS) that is suitable for molding. The characteristic of these materials is a tri-block structure, where a mid-block determines the difference between the styrene based end-blocks. Due to a saturated mid-block without double bonds, the material exhibits excellent UV-, ozone and weathering resistance. The two end-blocks consist of polystyrene domains, which are hard at room temperature but becomes softened and permit flow in the presence of heat. These domains act as physical cross-links between the mid-blocks to form a highly elastic continuous network. At room temperature, the mid-block is soft and elastic. The thermoplastic styrene based block-copolymer melts and flows at high temperatures, but regains its original structure and stability when cooled to ambient indoor and outdoor temperatures at which the liner is worn by the user. Service temperatures (indoor and outdoor) may range between approximately −40° C. to about +60° C. e.g.

The desired material properties in a liner blank according to this invention is advantageously characterized by a durometer ranging from about 5–40 Shore A, an elongation at break of about 600–1200%, a service temperature range of about −40° to about +60° C. a shrinkage of about 3% or less, and a processing temperature of about 200° C. in injection molding. A commercial product that meets the desired material properties is, e.g., the DRYFLEX© 500120 grade material from Nolato Elastoteknik, Torekov (SE).

As the customized liner blank now is imprinted with the shape of the copy, or in other the words the shape of the amputation stump, a smooth and equally applied compression is achieved about the entire amputation stump in the service position, when wearing the elastic liner, which in this manner provides a good suspension without locally applying pressure stresses. The stretching applied when donning the customized liner also is equal in all portions, resulting in even and proportionately small loss of entropy, in other words the liner maintains itself soft and elastic in all portions, which considerably decreases the risk of the wearer being chafed. To obtain a good and safe fixation between the soft inner liner and a hard outer socket the soft inner liner may be provided with a distal attachment device that is threaded onto different holders available on the market. An example of a distal holder is diagrammatically demonstrated in FIG. 12.

Figure 1:
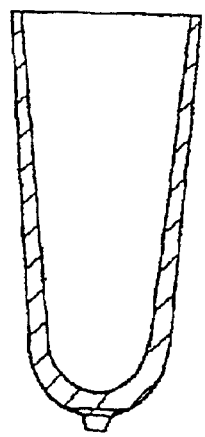
Figure 2:
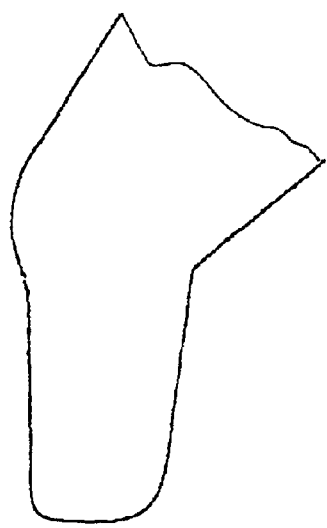
Figure 3:
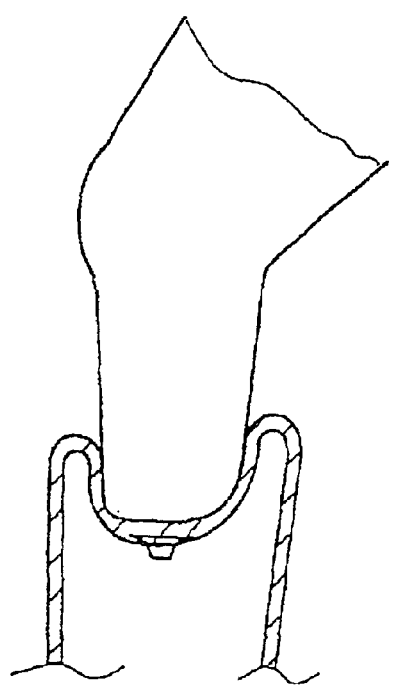
Figure 4:
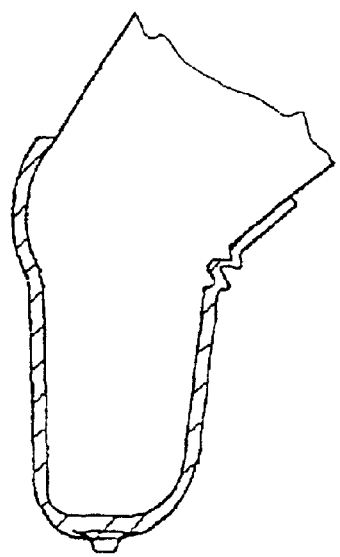
FIG. 4 shows an elastic liner according to the state of the art in a service position about the amputation stump.
Figure 5:
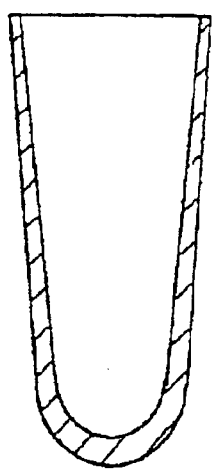
FIGS. 5 and 6 show embodiments of the liner blank of the present invention before thermoforming.
Figure 6:
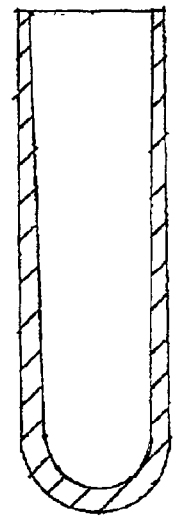

Another advantage is that the liner member according to the present invention may be formed after e.g. a flexed (bent) knee which makes it easy to avoid the folds which otherwise will appear at the back of the knee in a sitting position, compare for instance FIG. 4 and FIG. 7.

Still another advantage of a semi-finished liner blank according to the present invention is that it is not necessary to hold so many sizes in stock, since the size of the liner may easily be adapted by applying heat.

If for instance a stress-relief is desired around prominences, such a stress-relief may be simply achieved by using an additional piece of same material that is attached to the outer surface of the soft liner, whereby this accomplishes a locally thicker area of the liner. If it is desirable that the entire liner should be thicker it is simply possible to put a first liner blank and a second liner blank into each other and heat or glue these together. This also results, if a liner having a better scratch and abrasion strength is desirable in a particular application, that it is also possible to attach a somewhat harder liner of similar material to an inner soft elastic liner. Thus, this gives a softer liner towards the skin and a harder outer surface with increased capacity to withstand wear.

Additionally it is also possible to mix heat conducting material in the soft liner, which thereby will not be so warm. By mixing color particles in the thermoplastic elastomer material of the liner blank the liner may simply be colored, instead of being transparent, e.g. For an improved aesthetic appearance, enhanced resistance to wear or reduced friction, an elastic fabric skin may be applied on the exterior of the soft liner blank.

An advantage of the thermoplastic liner blank according to the present invention is that it is simple to afterwards perform small adjustments. If the amputation stump somewhat changes its appearance, the corresponding changes are performed to the earlier copy and the liner is again placed on the copy and heated, whereby after cooling it will maintain the new shape and regain the inherent elasticity of the elastic material.

What is claimed is:

1. A prosthetic liner blank, having an open proximal end and a closed distal end, provided for customizing to an individual user by thermoforming on a positive copy of the residuum of an amputee's arm or leg, the liner blank comprising:

a thermoplastic material suitable for molding and having a material composition allowing thermoforming, while maintaining elasticity in the thermally applied and remaining shape at service temperatures, ranging up to about +60° C., the thermoplastic material having a heat conducting material admixed therewith, the liner blank being a hollow, seamless and generally rotation symmetric element having a radial dimension, said radial dimension of the rotation symmetric element being dimensioned to accommodate all radii included in the positive copy, and the customized liner blank being imprinted with the shape and sectional profiles of the positive copy.

2. The liner blank of claim 1, wherein said radius of the rotation symmetric liner blank is over-dimensioned relative to any radius included in the positive copy, and the customized liner blank being contracted to the shape and sectional profiles of the positive copy.

3. The liner blank of claim 1, wherein said radius of the rotation symmetric liner blank is under-dimensioned relative to any radius included in the positive copy, and the customized liner blank being expanded to the shape and sectional profiles of the positive copy.

4. The liner blank of claim 1, wherein said radius of the rotation symmetric liner blank is dimensioned relative to the radii included in the positive copy such that the customized liner blank being contracted and expanded, respectively, to the shape and sectional profiles of the positive copy.

5. The liner blank of claim 1, wherein the thermoplastic material is a styrene based block-copolymer.

6. The liner blank of claim 5, wherein the thermoplastic material is a styrene-ethylene-butadiene-styrene block-copolymer.

7. The liner blank of claim 6, the thermoplastic material having a durometer ranging from about 5 to about 40 Shore A, an elongation at break of about 600% to about 1200%, and a service temperature ranging from about −40° to about +60° C.

8. The liner blank of claim 1, wherein a wall thickness of the rotation symmetric liner blank is reducing from the distal end towards the proximal end thereof.

9. The liner blank of claim 1, wherein the radius of the rotation symmetric liner blank is linearly reducing from the proximal end towards the distal end thereof.

10. The liner blank of claim 1, further comprising an outer layer of textile fabric.

11. The liner blank of claim 1, further having color pigments admixed with the thermoplastic material.

* * * * *